United States Patent
Murtazin et al.

(10) Patent No.: US 9,892,900 B2
(45) Date of Patent: Feb. 13, 2018

(54) APPARATUS AND METHOD FOR IMPROVING THROUGHPUT IN SPECTROMETRY

(71) Applicant: Thermo Fisher Scientific (Bremen) GmbH, Bremen (DE)

(72) Inventors: Ayrat Murtazin, Bremen (DE); Alexander Makarov, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 14/434,891

(22) PCT Filed: Oct. 4, 2013

(86) PCT No.: PCT/EP2013/070747
§ 371 (c)(1),
(2) Date: Apr. 10, 2015

(87) PCT Pub. No.: WO2014/056807
PCT Pub. Date: Apr. 17, 2014

(65) Prior Publication Data
US 2015/0255262 A1 Sep. 10, 2015

(30) Foreign Application Priority Data
Oct. 11, 2012 (GB) .................................. 1218247.3

(51) Int. Cl.
*H01J 49/10* (2006.01)
*B05B 7/00* (2006.01)
(Continued)

(52) U.S. Cl.
CPC .......... *H01J 49/105* (2013.01); *B05B 7/0075* (2013.01); *B05B 17/0607* (2013.01);
(Continued)

(58) Field of Classification Search
CPC ...................................................... H01J 49/105
(Continued)

(56) References Cited

U.S. PATENT DOCUMENTS 4,766,287 A * 8/1988 Morrisroe ............ H05H 1/2475
219/121.48
5,345,079 A * 9/1994 French ................ G01N 30/7273
250/282

(Continued)

FOREIGN PATENT DOCUMENTS

| CN | 101767078 A | 7/2010 |
| CN | 102301242 A | 12/2011 |
| DE | 10153708 A1 | 5/2003 |
| JP | 08201294 A | 8/1996 |
| WO | WO 99/34400 A1 | 7/1999 |

OTHER PUBLICATIONS

Murtazin et al., "Investigation of sample introduction- and plasma-related matrix effects in inductively coupled plasma spectrometry applying single analyte droplet and particle injection," Spectrochimica Acta Part B, 67, 3-16, 2012.

*Primary Examiner* — Tarifur Chowdhury
*Assistant Examiner* — Omar Nixon
(74) *Attorney, Agent, or Firm* — David A. Schell

(57) ABSTRACT

The invention provides a method and apparatus for improving throughput in spectrometry, the method comprising the steps of loading sample-containing liquid into a liquid injection device through a first outlet in the injection device, and ejecting at least some of the sample-containing liquid from the liquid injection device either in the form of droplets or in the form of a jet which subsequently breaks up into droplets due to instability; characterized by the sample ejection being through the first outlet of the liquid injection device in a direction such that the sample-containing fluid enters an inlet of a torch.

24 Claims, 1 Drawing Sheet

(51) Int. Cl.
*B05B 17/06* (2006.01)
*G01N 21/71* (2006.01)
*G01N 21/73* (2006.01)
*G01N 35/00* (2006.01)
*G01N 35/10* (2006.01)
*G01N 21/01* (2006.01)
*H01J 49/04* (2006.01)
*B05B 15/06* (2006.01)

(52) U.S. Cl.
CPC ........... *G01N 21/01* (2013.01); *G01N 21/714* (2013.01); *G01N 21/73* (2013.01); *G01N 35/0099* (2013.01); *G01N 35/1011* (2013.01); *H01J 49/0409* (2013.01); *H01J 49/0445* (2013.01); *B05B 15/065* (2013.01)

(58) Field of Classification Search
USPC ......................................................... 356/316
See application file for complete search history.

(56) References Cited

U.S. PATENT DOCUMENTS

| | | | | |
|---|---|---|---|---|
| 5,429,010 | A | * | 7/1995 | Lohndorf .................... B25J 9/04 73/864.31 |
| 5,867,262 | A | * | 2/1999 | Etoh ........................ G01N 35/08 250/288 |
| 2003/0156282 | A1 | | 8/2003 | Komatani et al. |
| 2010/0317118 | A1 | * | 12/2010 | Masujima ................ G01N 27/62 436/63 |
| 2011/0108726 | A1 | * | 5/2011 | Hiraoka ................. H01J 49/165 250/282 |
| 2011/0195519 | A1 | * | 8/2011 | Sturgeon .................. B01D 1/065 436/181 |
| 2012/0039771 | A1 | | 2/2012 | Utsugi et al. |
| 2012/0174650 | A1 | * | 7/2012 | Ariessohn ................. B08B 3/12 73/23.2 |

* cited by examiner

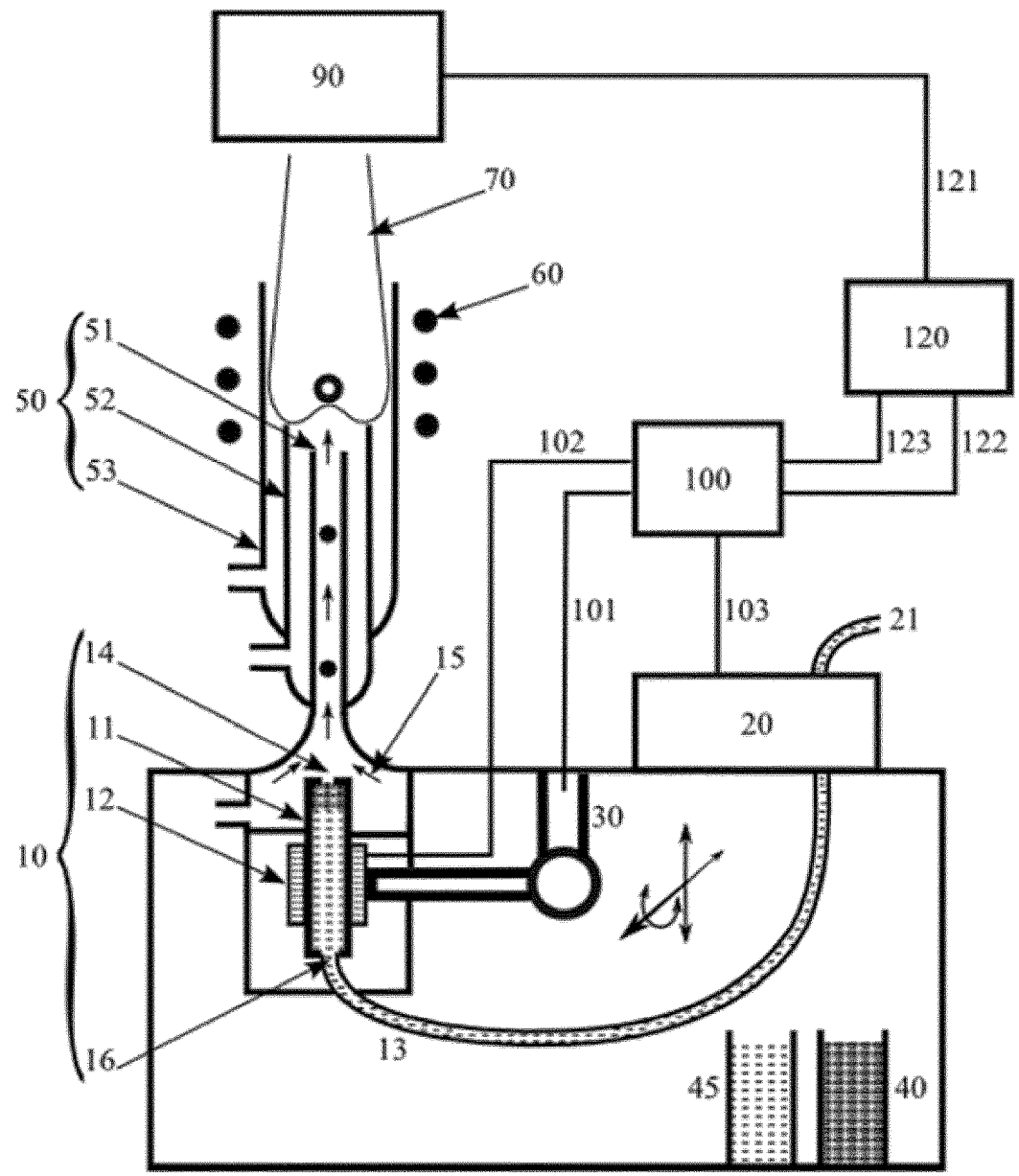

APPARATUS AND METHOD FOR IMPROVING THROUGHPUT IN SPECTROMETRY

FIELD OF THE INVENTION

This invention relates to the field of spectrometries in which droplets of sample-containing liquid are introduced into an optically-exciting or ionizing device immediately prior to analysis. The invention relates, for example, to spectrometries which utilize microwave induced plasma (MIP), inductively coupled plasma (ICP) and flames, applying to MIP and ICP optical emission spectrometry, to MIP and ICP mass spectrometry, and to atomic absorption spectrometry (AA) and atomic fluorescence spectroscopy (AFS). In particular it relates to the injection of liquid samples into a plasma or flame and is particularly relevant to the use of micro-dispensers as the injection means.

BACKGROUND OF THE INVENTION

Plasma optical emission spectrometry and plasma mass spectrometry are well known techniques for the analysis of trace elemental concentrations in liquids. The plasma may be formed using microwaves or by using an inductively-coupled system, both being examples of atmospheric-pressure plasmas. Typically detection limits extend to ppb levels for ICP-OES and ppt levels for ICP-MS. AA and AFS are also well known techniques utilizing a flame for atomizing sample material and all these techniques are often used in conjunction with one another in the laboratory.

In all these types of spectrometer, liquid samples are usually diluted and aspirated using a nebulizer or some form of droplet generator, being propelled out of an outlet of the nebulizer or droplet generator into an inert or flame gas stream which carries droplets of the sample-containing liquid into a torch and thereby into the plasma or flame. There are many different designs of torch, but as an example, in ICP-OES and ICP-MS the torch usually comprises three open-ended concentric cylindrical glass tubes along which inert gas streams are fed, the gas usually being argon. The liquid droplets are passed into the upstream end of the innermost cylinder of the torch, whilst additional inert gas is fed into the outer two glass tubes. At the downstream end of the tubes, a coil surrounds the torch and RF current typically at 27 MHz or 40 MHz is driven through the coil. A plasma discharge is initiated in the argon gas within the plasma torch in the vicinity of the coil. The sample-containing droplets are carried along the central channel of the torch and into the plasma discharge. The plasma discharge is sufficiently hot to cause the droplets of liquid entering the plasma to be progressively vaporized, atomized and then partially ionized. Atomized and ionized material is excited and relaxes to emit characteristic wavelengths of light detected by the optical spectrometer in the case of ICP-OES, and ionized material is directed into a vacuum system, through an ion optical system and a mass analyser in the case of ICP-MS. Similar torch arrangements are used in MIP spectrometry; AA and AFS use somewhat differently designed torches.

Typically the sample-containing liquid is formed into a stream of droplets using a nebulizer utilizing a stream of argon gas. Nebulizers produce droplets with a wide range of sizes. However both plasmas and flames are inefficient at dissociating large droplets and these are usually excluded by the use of a spray chamber placed between the nebulizer and the torch. The spray chamber filters the stream of droplets by causing the flow to follow a tortuous path such that the larger droplets impinge upon surfaces in the spray chamber and are drained away, smaller droplets being carried by the flow of gas into the torch. In the cases of ICP-OES and ICP-MS it is well known that only 1-2% of the nebulized sample-containing liquid is in the form of sufficiently small droplets suitable for processing within the torch, and that this form of sample introduction is therefore inefficient.

Various different types of droplet generators have been investigated in order to overcome this problem, and in order to facilitate the analysis of very small volumes of sample solution. Early attempts were made to create a single-droplet generator for flame analytical spectrometry utilizing a continuous fluid jet micro-droplet generator by G. M. Hieftje and H. V. Malmastadt (Analytical Chemistry, Vol. 40, pp. 1860-1867, 1968). Later a vibrating orifice monodisperse aerosol generator was used for investigation of airborne particles by ICP-OES and ICP-MS (H. Kawaguchi et al., Spectrochimica Acta, vol. 41B, pp. 1277-1286, 1986, T. Nomizu et al., Journal of Analytical Atomic Spectrometry, vol. 17, pp. 592-595, 2002).

The ability to produce droplets one at a time and thereby more completely control the droplet ejection process—so-called "droplet-on-demand" techniques—have long been seen as desirable. An early generator with this capability designed principally for inkjet printing was a piezoelectrical droplet generator (U.S. Pat. No. 3,683,212). With this generator no pressurized liquid supply is necessary (though pressurization may be used), and the time at which droplets are ejected together with the size of the droplets may be controlled by the application of an electrical pulse to the piezoelectric element. Such a droplet generator was employed to create a stream of droplets containing sample material, the droplets being passed through an oven so as to make the droplet evaporate to complete or partial dryness before injection into an ICP in order to study oxide ion formation (J. B. French, B. Etkin, R. Jong, Analytical Chemistry, Vol. 66, pp. 685-691, 1994). This coupling of the piezoelectric droplet generator and oven was termed the monodisperse dried microparticulate injector (MDMI) and such systems have been used in other studies (J. W. Olesik and S. E. Hobbs, Analytical Chemistry, vol. 66, pp. 3371-3378, 1994; A. C. Lazar and P. B. Farnsworth, Applied Spectroscopy, vol. 53, pp. 457-470, 1999; A. C. Lazar and P. B. Farnsworth, Applied Spectroscopy, vol. 51, pp. 617-624, 1997).

Use of the piezoelectric droplet generator without the desolvation in an oven has been successfully implemented as a sub-nanoliter sample introduction technique for Laser-Induced Breakdown Spectroscopy and Inductively Coupled Plasma Spectrometry (S. Groh et al., Analytical Chemistry, vol. 82, pp. 2568-2573, 2010; A. Murtazin et al., Spectrochimica Acta, vol. 67B, pp. 3-16, 2012).

Investigations of the use of thermal inkjet droplet generators for use as a sample injector in ICP spectrometry have also been performed (J. O. Orlandini v. Niessen et al., Journal of Analytical Atomic Spectrometry, vol. 26, pp. 1781-1789, 2011).

Micro-dispensers such as these have been used for fundamental studies relating to processes in plasmas, and for the purposes of improving sample utilization and control over sample introduction, but relatively little has been written concerning sample throughput.

Due to the increasingly routine use of spectrometry, sample throughput has become one of the most important requirements as it is this which ultimately determines the cost-per-analysis in routine applications. With the increased sensitivity of instrumentation and automated sample handling, sample throughput is largely limited not by the sample introduction or analysis time but rather by memory effects caused by deposition of material from the previous sample on components of the sample introduction system and spectrometer. Due to the increased sensitivity of the spectrometers and their ultimate detection limits, material deposited upon the sample introduction system is gradually washed away during a "wash" cycle and typically at least 40-60 seconds is needed after each sample to reduce memory effects below an acceptable threshold. It is known that deposition of sample material upon the surfaces of the glassware of the torch, the nebuliser, the spray chamber and the sample line are of particular importance. Direct injection nebulizers were used to reduce memory effects as they eliminated some of these components but they produced aerosols with droplets with very large ranges in size and density and thus compromised performance of the technique (WO9934400A1, WO2005062883A2, WO2005079218A2, US2006087651 A1, US2007299561 A1).

The reduction of dead volumes within a micro-dispenser was considered an important need by Groh et. al. (Anal. Chem., V. 82, No. 6, pp 2568-2573, 2010) and interfacing a monodisperse droplet generator to a 'lab-on-a-chip' was suggested, in order to address washout issues and to enable analysis of ultra-low sample volumes.

A 0.1 mL reservoir was utilised by Orlandini (J. Anal. At. Spectrom., 2011, 26, 1781-1789). Filling and rinsing of the reservoir was performed manually using micro-pipettes. A rinsing cycle repeated five times using deionised water was found necessary to regain background signal level after applying 1 mgL$^{-1}$ sample concentrations with a multi-nozzle inkjet cartridge. Sample solution came in contact with metallic and non-metallic components and sample contamination and elevated background levels were of concern.

Washout times in excess of 30 s were expected in a MDMI system, but due to diffusion and mixing, 100 s washout times were observed to reduce a background by 99%, which was considered long compared to other nebulisers (Lazar and Farnsworth, Applied Spectroscopy, V. 51, No. 5, pp 617-624, 1997).

Against this background, the present invention has been made.

SUMMARY OF THE INVENTION

The invention provides a method of improving throughput in spectrometry comprising the steps of loading sample-containing liquid into a liquid injection device through a first outlet in the injection device, and ejecting at least some of the sample-containing liquid from the liquid injection device either in the form of droplets or in the form of a jet which subsequently breaks up into droplets due to instability; characterized by the sample ejection being through the first outlet of the liquid injection device in a direction such that the sample-containing fluid enters an inlet of a torch.

The invention further provides apparatus for sample injection into a torch comprising a manipulator and a liquid injection device, the liquid injection device comprising a first outlet; characterized in that the manipulator is arranged so that, in use, it can move the liquid injection device from a first position to a second position, the first position being such that the first outlet is aligned so that ejected liquid may enter the torch, the second position being such that the first outlet is positioned so as to be in fluid communication with a vessel for holding a sample-containing liquid.

As described above, in routine applications, sample throughput is largely limited not by the sample introduction or analysis time but rather by memory effects caused by deposition of material from the previous sample on components of the sample introduction system and spectrometer. A critical element requiring washout is the liquid injection device and the method and apparatus of the present invention addresses the washout process of the liquid injection device in order to improve the throughput of the spectrometry utilising the injector. The method and apparatus of the invention may be applied to a wide variety of liquid injection devices, including piezo-actuated droplet generators, thermal inkjet devices, monodisperse dried microparticulate injectors, vibrating orifice monodisperse aerosol generators, continuous fluid jet microdroplet generators, and flow focusing injectors amongst others, and it is anticipated that the methods and apparatus will be applicable to as-yet unknown types of liquid injection device. Whilst widely applicable, the method and apparatus of the invention confer additional advantages where the liquid injection device is a low flow device, such as a microdroplet dispenser, as will be further described.

Whilst considering ways in which to overcome limitations on sample throughput due to memory effects in the liquid injection device, the inventors realized that advantages are gained by minimizing the quantity of sample to which the liquid injector surfaces are exposed. However liquid injection devices possess minimum volumes which must be filled with liquid in order for the injection device to properly function. In prior art uses of these injectors, sample-containing liquid is supplied to the injector via a conduit and is introduced into the injector via an inlet, and the sample-containing liquid is fed through the injector to an outlet from which droplets or jets of the liquid are ejected. Hence the whole internal volume of the injector (as well as the liquid supply conduit) is exposed to the sample-containing liquid, and the whole internal volume must be emptied of a first sample-containing liquid before a second sample-containing liquid can be introduced without sample mixing occurring. Furthermore, the entire internal surfaces of the injector must be washed clean before the second liquid is introduced, if memory effects are to be minimized. As noted above, this process typically takes many tens of seconds, due to the increased sensitivity of modern spectrometry systems. The invention addresses this problem by reducing the quantity of sample-containing liquid which enters the injector thereby reducing the volume occupied by the sample-containing liquid and internal surface area of the injector with which the sample-containing liquid comes in contact. This is achieved by avoiding the prior art method of loading the sample-containing liquid into the injector through an inlet and then feeding the liquid through the injector to an outlet. The invention also enables the liquid supply conduit to be eliminated further reducing the surface area brought in contact with the sample-containing liquid. The invented method and apparatus enables sample-containing liquid to be drawn into a first outlet of the liquid injection device and then propelled back out the first outlet and into the spectrometer. By this, the quantity of sample-containing liquid loaded into the injector may be minimized to a volume only slightly greater than the volume to be passed into the spectrometer, and the sample-containing liquid only occupies a volume and contacts internal surfaces of the liquid injection device at and close to the first outlet. Sample containing liquid need not contact any liquid supply conduit. Hence both the quantity of a first sample-containing liquid which must be expelled from the injector, and the internal surface area of the injector requiring washout, before a second sample-containing liquid is introduced into the injector, are greatly reduced. Furthermore, no liquid supply conduit requires washout.

The method and apparatus are particularly suited to low flow sample injection devices which are slow to expel liquids. Such injectors are slow to both empty previously loaded sample-containing liquid and to expel wash liquid used to clean the internal surfaces of the injector. Low flow injection devices are becoming increasingly important in the spectrometries which utilize liquid droplet streams as they may typically enable streams of smaller droplets of the sample-containing liquid to be produced, and they may create droplets having a more uniform size distribution, both of which are becoming increasingly desirable for high efficiency utilization of small sample volumes.

The term sample-containing liquid is herein used to mean either a liquid which entirely consists of a sample, or a liquid which comprises a sample (such as slurries or nanoparticles in suspension). Typically samples are diluted with a solvent but in some instances samples may be of a form which allows them to be directly injected into the spectrometer without dilution and both forms may be used in the invented method and apparatus.

In the method of the invention, sample-containing liquid is loaded into the liquid injection device via a first outlet. The outlet comprises a passage or orifice. The action of loading the sample into the liquid injection device may be accomplished in many ways, but in preferred embodiments, the sample-containing liquid is loaded by drawing it into the liquid injection device by applying suction to a second outlet of the liquid injection device. The suction may be applied by any means, and as used herein any such device is termed a pump. The suction is preferably applied to a fluid contained within the liquid injection device. Preferably the fluid is a liquid, termed herein a buffer liquid. More preferably the fluid is a pure liquid that does not mix with the sample-containing liquids to be analysed, and hence may be a liquid such as an oil, preferably a fluorocarbon oil, which does not mix with water, thereby reducing mixing with sample-containing liquids due to diffusion and keeping a part of the internal surface area of the liquid injection device which is contacted by sample-containing liquid free from contaminants due to hydrophobisation of the internal surfaces of the injection device. Alternatively, or in addition, a small gas bubble may be disposed between the buffer liquid and the sample-containing liquid thereby separating the two different liquids and preventing mixing of the two different liquids. A gas bubble may be so disposed between the buffer liquid and the sample-containing liquid by applying suction to the second outlet of the liquid injection device for a short period of time whilst the first outlet of the liquid injection device is exposed to the gas immediately before bringing the first outlet of the liquid injection device into in fluid communication with the sample-containing liquid. The gas may be any suitable gas, including air or an inert gas. To further minimize washout, the internal surfaces of the liquid injection device which come into contact with sample-containing liquid and the area around the first outlet may be coated with a hydrophobic coating. The suction acting upon the fluid in the injector causes sample-containing liquid to be drawn into the liquid injection device through the first outlet, the first outlet of the liquid injection device being at that time in fluid communication with a source of the sample-containing liquid. Preferably the source of the sample-containing liquid is a vessel containing a quantity of the sample-containing liquid. As used herein the term vessel includes any means for containing a liquid, including but not limited to chambers and conduits. Preferably each sample is contained within a separate vessel or conduit in which case no common liquid supply conduit comes in contact with sample-containing liquid and therefore no liquid supply conduit requires washout between samples. Prior to the process of loading a quantity of sample-containing liquid into the liquid injection device through a first outlet in the injection device, the liquid injection device is placed in fluid communication with the source of the sample-containing liquid, which may be accomplished by moving the source of the sample-containing liquid or it may be accomplished by moving the liquid injection device, or by a combination of these movements. Preferably the liquid injection device is placed in fluid communication with the source of the sample-containing liquid by moving the liquid injection device.

Having loaded a quantity of sample-containing liquid into the liquid injection device through a first outlet in the injection device a quantity of the sample-containing liquid that has been loaded into the liquid injection device is then ejected from the liquid injection device either in the form of droplets or in the form of a jet which subsequently breaks up into droplets due to instability. Many preferred liquid injection devices comprise microdroplet dispensers which eject liquid in the form of single droplets. Some preferred liquid injection devices comprise microdroplet dispensers which eject liquid in the form of a microjet or capillary which subsequently breaks up into droplets due to instability. An example of such a liquid injection device includes a flow focusing injector, an example of which is described in U.S. Pat. No. 6,119,953. The term jet as used herein includes microjets, capilar jets and capillaries. Preferably the liquid injection device is a micro-dispenser configured to eject single droplets less than 100 μm in diameter.

The ejection of liquid from the liquid injection device either in the form of droplets or in the form of a jet which subsequently breaks up into droplets due to instability is through the first outlet of the liquid injection device in a direction such that the sample-containing fluid enters an inlet of a torch. Preferably the ejection of liquid from the liquid injection device is aligned with the axis of the inlet of the torch. In some embodiments a desolvator is located between the first outlet of the liquid injection device and the torch, in which case the ejection of liquid from the liquid injection device is aligned with the axis of an inlet of the desolvator so that ejected liquid enters the desolvator before passing on to enter the inlet of the torch. Embodiments may instead or in addition comprise a gas entrainment device located between the liquid injection device and the torch, in which case the ejection of liquid from the liquid injection device is directed so as to enter an inlet of the gas entrainment device so that ejected liquid enters the gas entrainment device before passing on to enter the inlet of the torch. When used together, the desolvator and the gas entrainment device may be positioned in either order. The axes of the desolvator and the gas entrainment device may or may not be coaxial with the axis of the inlet of the torch, depending upon the configurations of the desolvator and gas entrainment device.

Preferably, preceding the step of loading sample-containing liquid into a liquid injection device through a first outlet in the injection device, the liquid injection device is moved from a first position to a second position; and preferably immediately preceding the step of ejecting at least some of the sample-containing liquid from the liquid injection device, the liquid injection device is moved from the second position to the first position; the first position being such that the first outlet is aligned with the inlet of the plasma torch or the inlet of a desolvator or the inlet of a gas entrainment device; the second position being such that the first outlet is in liquid communication with a quantity of sample-containing liquid.

Preferably the method further comprises ejecting substantially all unused previously loaded sample-containing liquid from the liquid injection device through the first outlet to waste. Preferably the liquid injection device is moved to a third position immediately preceding the step of ejecting substantially all unused previously loaded sample-containing liquid from the liquid injection device through the first outlet to waste.

The method preferably comprises the further step of rinsing the liquid injection device by positioning the first outlet of the liquid injection device in fluid communication with a quantity of rinsing agent and loading rinsing agent into the first outlet and ejecting rinsing agent out of the first outlet. Preferably the liquid injection device is moved to a fourth position immediately preceding the step of rinsing the liquid injection device by positioning the first outlet in fluid communication with a quantity of rinsing agent and loading rinsing agent into the first outlet and ejecting rinsing agent out of the first outlet.

Preferred embodiments comprise a liquid injection device and a conduit having one end attached to the second outlet of the liquid injection device, the conduit having a second end attached to a pump the pump being arranged so that in use it can both provide suction (negative pressure) or positive pressure to the conduit. Such embodiments may then utilize the pump to provide suction to the second outlet of the liquid injection device in order to load sample-containing liquid into the liquid injection device through the first outlet, in accordance with the method of the invention. These embodiments may also utilize the pump to provide a positive pressure to the conduit so as to drive a buffer liquid into the liquid injection device, and thereby to eject substantially all unused previously loaded sample-containing liquid from the liquid injection device through the first outlet to waste. A quantity of buffer liquid may also be ejected from the first outlet of the liquid injection device to affect a washout. The pump may also provide negative pressure to the second outlet in order to load into the liquid injection device a quantity of rinsing agent through the first outlet and thereafter eject the said rinsing agent out of the first outlet by the application of positive pressure to the second outlet.

In preferred embodiments, the liquid injection device is moved between the first and the second positions using a manipulator. Preferably the manipulator is arranged so that, in use, it can move the liquid injection device from a first position to a second position, the first position being such that the first outlet is aligned so that ejected liquid may enter the torch, the second position being such that the first outlet is positioned so as to be in fluid communication with a vessel. Preferably the liquid injection device is moved to the third position and/or to the fourth position using a manipulator, more preferably the same manipulator that is used to move the liquid injection device to the first and second positions. Where a single manipulator is used, preferably the manipulator is arranged so that, in use, it can move the liquid injection device from the first position to a third position and it can move the liquid injection device from the third position to a fourth position. Preferably the manipulator is arranged move the liquid injection device between any of the first, second, third and fourth positions in any order. Preferably the manipulator is arranged to move any of a plurality of similar or dissimilar liquid injection devices between any of the first, second, third and fourth positions, in any order.

Preferably the apparatus further comprises a controller arranged so that in use it may control the apparatus. Preferably the apparatus further comprises a computer having an input for receiving data from the spectrometer indicative of the progress of sample analysis, and an output for outputting control signals to the controller and wherein the computer is programmed with a program comprising one or more modules of program code for deriving control signals to output to the controller. In preferred embodiments the computer is provided with an input for receiving data which includes information about individual emitted droplets, e.g. data which is provided either from electronics or a computer controlling droplet generation from the liquid injection device such as an electrical signal from a droplet generator. Preferred embodiments of the invention also comprise a computer readable medium carrying a computer program, the program having modules of program code for carrying out the method of the invention.

Embodiments of the method of the present invention may provide additional gains in throughput by utilizing more than one liquid injection device. In such embodiments the liquid injection device is one of a plurality of similar or dissimilar liquid injection devices each able to be arranged to eject sample-containing liquid in a direction such that the sample-containing fluid enters the inlet of the plasma torch. In such embodiments a first liquid injection device may be controlled so as to perform the steps of (a) loading sample-containing liquid into a liquid injection device through a first outlet in the injection device, and (b) ejecting at least some of the sample-containing liquid from the liquid injection device either in the form of droplets or in the form of a jet which subsequently breaks up into droplets due to instability, characterized by the sample ejection being through the first outlet of the liquid injection device in a direction such that the sample-containing fluid enters an inlet of a torch, and a second liquid injection device may be controlled so as to perform step (b) at a time whilst the first liquid injection device is performing step (a). By this means the time between the introduction of different samples into the torch of the spectrometer is reduced and the throughput thereby increased. Additional improvements may be obtained by performing steps of ejecting substantially all unused previously loaded sample-containing liquid from the liquid injection device through the first outlet to waste whilst rinsing another liquid injection device with rinsing agent. Where embodiments of the invention comprise four liquid injection devices, whilst a first liquid injection device performs step (a), a second liquid injection device may be performing step (b), a third liquid injection device may be ejecting substantially all unused previously loaded sample-containing liquid from the liquid injection device through the first outlet to waste, and a fourth liquid injection device may be loading and ejecting rinsing agent.

The method and apparatus of the present invention apply to the field of spectrometry and preferably to analytical atomic spectrometry. As already described above, the torch preferably forms part of a microwave induced plasma or inductively coupled plasma optical emission or mass spectrometer, or an atomic absorption spectrometer, and sample-containing liquid ejected from the injection device enters the torch and is then analysed by the spectrometer. ICP optical emission and ICP mass spectrometry are particularly preferred spectrometric uses for the method and apparatus.

DESCRIPTION OF FIGURES

FIG. 1 is a schematic diagram showing one embodiment of the present invention.

DETAILED DESCRIPTION OF PREFERRED EMBODIMENTS

FIG. 1 is a schematic diagram showing one embodiment of the present invention. In this embodiment a piezoelectric microdispenser is used as the liquid injection device and the torch is suitable for use with an ICP, being shown in conjunction with ICP spectrometer.

Liquid injection device comprising single-droplet microdispenser (SDMD) 10 comprises liquid-filled glass tube 11, outer piezoelectric element 12 (a cylindrical shape is shown), a first outlet 14 and a second outlet 16. Second outlet 16 is in fluid communication with a conduit 13 containing buffer liquid, conduit 13 being connected to the second outlet at one end and being connected at a second end to pump 20. Examples of such microdispensers are manufactured, for example, by Microdrop GmbH (see patent DE10153708), MicroFab (U.S. Pat. No. 6,378,988, U.S. Pat. No. 6,367,925), GeSiM (EP1314479). Microdispensers of this type may be in the form of single liquid injection devices, or as an array of liquid injection devices as will be further described. A single liquid injection device is shown in FIG. 1.

Manipulator 30, liquid injection device 10 and pump 20 are controlled by controller 100 via control lines 101, 102, 103 respectively, and controller 100 is in communication with computer 120. Computer 120 includes an input 121 for receiving data from the spectrometer 90 indicative of the progress of sample analysis and an output 122 for outputting control signals to controller 100, and computer 120 is programmed with a program comprising modules of program code for deriving control signals to output to the controller 100. Computer 120 is provided with an input 123 for receiving data from controller 100 which includes information about individual emitted droplets.

Liquid injection device 10 is shown in a first position in FIG. 1. Manipulator 30 is used to move the liquid injection device 10 from the first position to a second position (not shown), so that the first outlet 14 is in fluid communication with vessel 40 which contains sample-containing liquid. In this embodiment, the first outlet 14 of liquid injection device 10 is inserted into vessel 40 by manipulator 30 to affect the liquid communication. Pump 20 is activated to apply negative pressure to conduit 13 causing buffer liquid to be withdrawn from liquid injection device 10 through second outlet 16, and this causes sample-containing liquid to be drawn into liquid injection device 10 through first outlet 14. Once a sufficient quantity of sample-containing liquid has been loaded into liquid injection device 10 for subsequent analysis (preferably 5-50 microliters), pump 20 is stopped. The amount of sample-containing liquid may be just enough for the anticipated analysis requirements, but should be less than that which would cause mixing of the sample-containing liquid with buffer liquid. Manipulator 30 then moves the liquid injection device 10 from the second position to the first position. The time to perform the operations described so far in relation to FIG. 1 is 5-10 seconds.

Upon reaching the first position, the liquid injection device 10 is activated to eject some of the sample-containing liquid from the liquid injection device through the first outlet 14, in the form of droplets. The activation comprises an electric pulse which is applied to piezoelectric element 12 and this initiates a shock wave in the sample-containing liquid causing a micro-droplet of sample with typical dimensions 5-100 micrometers to be ejected from first outlet 14. The initial velocity of this droplet of several meters per second is sufficient to propel it into a flow of argon gas 15 which is generally concentric with the cylindrical glass tube 11. This flow of argon gas is known as an injection gas, passing into the injector tube 51 of the torch 50. Torch 50 also comprises auxiliary tube 52 and outer tube 53. Typically, torch 50 is made of quartz glass or ceramic elements. ICP coil 60 is used to couple RF power (typically, at 27 MHz) into plasma 70. The liquid injection device when in the first position is located so as to protrude into a tapered inlet end of injector tube 51 (but without causing discharge). The injection gas flow carries the droplet ejected from the liquid injection device through the injector tube 51 into ICP plasma 70 where it gets fully atomized and partially ionized. Excited atoms and ions emit photons characteristic of the elements in the sample and spectrometer 90 may comprise an optical spectrometer. Alternatively ions may be drawn into a vacuum system and pass into a mass spectrometer wherein their mass-to-charge ratio is determined and in this case spectrometer 90 comprises a mass spectrometer.

As sample utilization approaches 100% as opposed to 1-2% in traditional pneumatic nebulizers, only few microliters of sample is sufficient to get the same signal. For preferable droplet diameters of 50-70 μm this requires $10^4$–$5\times10^4$ droplets that could be provided within 5-25 seconds of SDMD operation at up to 2 kHz droplet ejection rate. Higher frequencies are possible but increase the chances of droplets merging. Additionally, the narrow temporal width of signal (<1-2 ms FWHM) allows the signal-to-noise ratio to be improved at lower repetition rates as signals from individual droplets do not overlap and could be acquired individually and in a gated manner.

Once a droplet leaves the SDMD 10, it never touches any surface again before entering the plasma 70 therefore memory effects within the torch 50 will be negligible. However, SDMD 10 itself might have its orifice 14 and its immediate surroundings contaminated by sample and therefore a thorough wash procedure is required. This is addressed by moving the SDMD 10 from the first position into a third position (which in this example is perpendicular to the plane of FIG. 1) using manipulator 30, and applying positive pressure to conduit 13 using pump 20, causing unused sample-containing liquid to be ejected from the SDMD 10 to waste. Additional buffer liquid is supplied from supply line 21 via conduit 13 which may serve to wash out the liquid injection device 10 and also to replenish the buffer liquid that partially filled the liquid injection device 10, eliminating the liquid that was in the vicinity of the interface between the sample-containing liquid and the buffer liquid. Once the sampling volume within liquid injection device 10 is drained many times over (e.g. by spraying 0.1-0.5 mL of liquid at flow rate 1-5 mL/min), SDMD 10 is ready for loading again, after some 10-20 sec. Prior to loading, it could be additionally rinsed in the optional rinse tube 45, e.g. for 10-15 seconds (this operation could be combined with draining). To accomplish this, manipulator 30 moves the liquid injection device 10 to a fourth position (not shown), so that the first outlet 14 is in fluid communication with vessel 45 which contains a rinsing agent. In this embodiment, the first outlet 14 of liquid injection device 10 is inserted into vessel 45 by manipulator 30 to affect the liquid communication. Pump 20 is activated to apply negative pressure to conduit 13 causing buffer liquid to be withdrawn from liquid injection device 10 through second outlet 16, and this causes rinsing agent to be drawn into liquid injection device 10 through first outlet 14. Once a sufficient quantity of rinsing agent has been loaded into liquid injection device 10 pump 20 is controlled so as to produce a positive pressure to conduit 13, ejecting the rinsing agent out of the first outlet 14 of liquid injection device 10. This process of loading and ejecting rinsing agent may be repeated. Washout efficiency may be further improved by applying electric pulses to piezoelectric element 12 during the rinsing procedure. The total wash time after every sample could thereby be reduced to 20-30 seconds (allowing also for 5-10 sec motion time of manipulator 30).

This wash time represents a 2-fold improvement over prior art methods of washout and is achieved using the invented method and apparatus by reducing the surface area which comes in contact with the sample-containing liquid. Further improvements may be made using the method and apparatus of the invention if additional liquid injection devices are utilized. In this case, multiple liquid injection devices may be arranged, for example, as linear or annular or radiating arrays of e.g. 8 or 12 or 16 SDMDs. Preferably an array of vessels containing rinsing agent is arranged to match the array of liquid injection devices and a further array of sample-containing vessels is arranged to match the array of liquid injection devices. Each SDMD is individually addressed by manipulator 30 (or optionally by a group of independent manipulators), and rinsing of a particular SDMD could start immediately after the end of ejecting sample-containing liquid and it could continue until the last SDMD has finished ejecting sample-containing liquid. Preferably the last SDMD contains the sample with the lowest concentration. Sample loading of all the liquid injection devices may be performed in parallel. This means that the analysis time per sample is:

$$T_a = (T_{preparation} + N*T_{sampling} + T_{rinsing} + T_{motion})/N = T_{sampling} + (T_{preparation} + T_{rinsing} + T_{motion})/N$$

where $T_{preparation}$ is the time to load sample-containing liquid into the liquid injection device, $T_{sampling}$ is the time to eject sample-containing liquid so that it passes into the inlet of the torch, $T_{rinsing}$ is the time to rinse the liquid injection device with rinsing agent, $T_{motion}$ is the time to move the liquid injection device between the various positions, and N is the number of liquid injection devices in the array.

Utilising this aspect of the invention the added overhead time per analysis is N times smaller than total 20-30 seconds above and may constitute only 2-3 seconds per sample for a sufficiently high number N of liquid injection devices. With independent manipulators, sampling from one SDMD could be done in parallel with rinsing of another and motion of the third therefore this overhead could be further reduced though at the expense of added complexity.

As noted above, the array of liquid injection devices may be an array of similar or dissimilar liquid injection devices. Different liquid injection devices may be preferred for different types of sample. Preferably all the liquid injection devices in the array are similar to one another.

A particularly preferred embodiment comprises an array of SDMDs each having an outer diameter <6 mm, preferably 3 mm, each having internal hydrophobic coating and each producing droplets with diameters of 50-70 μm at frequency 2000 Hz. The buffer liquid in conduit 13 is preferably distilled de-ionised water or the same solvent as used in the samples, or an oil which does not mix with water, for example such as a fluorcarbon oil. The argon gas flow in injector tube 51 is 0.2-0.3 L/min (lower than is usual for conventional nebulisers), the argon gas flow in auxiliary tube 52 is <1 L/min, the argon gas flow in the outer tube 53 is 10-15 L/min and the ICP forward power is 1-1.5 kW. The desired analysis time per sample is 15-20 sec (3-4 samples/min).

When utilizing the invention in optical ICP spectrometry it is important to take advantage of temporal structure of the signal, i.e. signal should be acquired only when material of each droplet is emitting optically. Flicker and shot noises of the background could be reduced thus improving signal-to-noise ratios. To aid in this, computer 120 is provided with an input 123 for receiving data from controller 100 which includes information about individual emitted droplets, which may include, for example, a timing signal as each droplet is emitted from the liquid injection device.

Though SDMD 10 is best operated in a vertical orientation so as to eject droplets in a vertical direction, it may also be operated in a horizontal orientation (as is typical for ICP-MS). For this, injector tube 51 should be made as short as possible (preferably <50 mm) and SDMD 10 shifted slightly upwards and preferably tilted by several degrees so that ejected droplets do not impinge upon the inner surface of the injector. In principle it is also possible to operate SDMD 10 with its orientation downwards.

Manipulator 30 could be based on any suitable commercial manipulator as is known in the art.

The apparatus and methods of the present invention may be used to deliver material from solid samples to the plasma or flame. This may be achieved by depositing one or more droplets of carrier liquid onto the solid sample surface utilizing the liquid injection device. Sample material may be transferred into the carrier liquid droplet by various means, including:

(i) Chemically dissolving the sample by using a carrier liquid which may be an acid or other reactive liquid; the chemical reaction may be assisted by heating, or the application of ultrasonic waves, for example;
(ii) Microextraction/desorption also assisted if necessary by ultrasonic waves, heating etc.;
(iii) Laser ablation of the solid sample surface using a laser beam directed through the droplet, or where the solid sample resides upon a transparent carrier plate, through the back of the carrier plate.

In all three examples, the carrier liquid droplet which is charged with solid sample material is then picked up and dispensed in the form of monodisperse droplets into the plasma or flame using the same or another liquid injection device.

Material from solid samples may also be delivered to the plasma via droplets dispensed from the liquid injection device of the present invention where the droplets do not contact the solid sample surface. In this case, particles of solid sample are ablated from the solid sample surface and impinge upon a stream of droplets dispensed from the liquid injection device and which are travelling in the vicinity of the solid sample surface on their way to plasma or flame. Ablation may be achieved by pulse heating, spark ablation, or laser ablation, for example.

By the above means, contamination of the solid sample material during its transfer into the carrier liquid is thereby minimized, there being no contact between the solid sample and any other liquids or solids. This also reduces memory effects as no separate sample preparation apparatus is involved such as vessels, tubing or pipettes, all of which must be cleaned after contact with each sample. Use of such sample preparation apparatus reduces the time available to analyse samples and hence the present invention provides improvements in throughput over prior art methods and apparatus. Furthermore, sampled material is not diluted by surrounding gas thereby improving the sensitivity of the analysis.

Nanoparticles may be suspended in bulk liquid carrier by bubbling gas containing the nanoparticles through the liquid carrier prior to dispensing using the liquid injection device. For example this may be used to suspend nanoparticles found in air by bubbling the air through a suitable carrier liquid, enabling analysis of the nanoparticles by the spectrometer.

Use of the liquid injection device of the present invention enables further optimizations of the spectrometer to be made. Various different torch designs are contemplated, such as a two tube torch, a torch of small axial length, a micro-torch, a low gas-consumption torch. The torch injector tube and the liquid injection device may be combined into one component both to minimize the distance between the sample introduction point and the plasma or flame; so as to simplify construction and eliminate tube joints, which may harbor contamination; and to facilitate the transport of larger droplets. The spectrometer optics may also be redesigned so as to image the far smaller signal emitting volume which results from the excitation of single microdroplets. Signal detection electronics may also be modified to make best use of the transient nature of the signals generated from single microdroplets, for example synchronous detection methods may be employed, and boxcar detection. These may be particularly applicable to ICP-MS.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to" and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

The invention claimed is:

1. A method of improving throughput in spectrometry comprising the steps of:
   a. loading sample-containing liquid into a liquid injection device through a first outlet in the injection device, and
   b. ejecting at least some of the sample-containing liquid from the liquid injection device either in the form of droplets or in the form of a jet which subsequently breaks up into droplets due to instability,
   characterized by the sample ejection being through the first outlet of the liquid injection device in a direction such that the sample-containing fluid enters an inlet of a torch; wherein immediately preceding step (a) the liquid injection device is moved from a first position to a second position, and wherein immediately preceding step (b) the liquid injection device is moved from the second position to the first position; the first position being such that the first outlet is aligned with the inlet of the plasma torch or the inlet of a desolvator or the inlet of a gas entrainment device; the second position being such that the first outlet is in liquid communication with a quantity of sample-containing liquid; wherein the liquid injection device is moved to a third position immediately preceding step (c) of ejecting substantially all unused previously loaded sample-containing liquid from the liquid injection device through the first outlet to waste.

2. The method of claim 1 wherein sample-containing liquid is drawn into the liquid injection device by applying suction to a second outlet in the liquid injection device.

3. The method of claim 2 wherein a buffer liquid is contained within the liquid injection device and the buffer liquid is sucked out of the second outlet so as to draw sample-containing liquid into the first outlet.

4. The method of claim 1 wherein the liquid injection device is moved between the first and the second positions using a manipulator.

5. The method of claim 1 comprising the further step (d) of rinsing the liquid injection device by positioning the first outlet of the liquid injection device in fluid communication with a quantity of rinsing agent and loading rinsing agent into the first outlet and ejecting rinsing agent out of the first outlet.

6. The method of claim 1 wherein the liquid injection device is moved to a fourth position immediately preceding step (d) of rinsing the liquid injection device by positioning the first outlet of the liquid injection device in fluid communication with a quantity of rinsing agent and loading rinsing agent into the first outlet and ejecting rinsing agent out of the first outlet.

7. The method of claim 1 wherein the liquid injection device is moved to the third position using a manipulator.

8. The method of claim 1 wherein the liquid injection device is a micro-dispenser configured to eject single droplets less than 100 um in diameter.

9. The method of claim 8 wherein the micro-dispenser is one of: a piezo-actuated droplet generator, a thermal inkjet device, a monodisperse dried microparticulate injector, a vibrating orifice monodisperse aerosol generator, a continuous fluid jet microdroplet generator, a flow focusing injector.

10. The method of claim 1 wherein the liquid injection device is one of a plurality of similar or dissimilar liquid injection devices each able to be arranged to eject sample-containing liquid in a direction such that the sample-containing fluid enters the inlet of the plasma torch.

11. The method of claim 10 wherein a first liquid injection device is controlled so as to perform steps (a) and (b), and wherein a second liquid injection device is controlled so as to perform step (b) at a time whilst the first liquid injection device is performing step (a).

12. The method of claim 1 wherein the torch forms part of a microwave induced plasma or inductively coupled plasma optical emission or mass spectrometer, or an atomic absorption spectrometer, or an atomic fluorescence spectrometer, and sample-containing liquid ejected from the injection device enters the torch and is then analyzed by the spectrometer.

13. A non-transitory computer readable medium carrying a computer program, the program having modules of program code for carrying out the method of claim 1.

14. Apparatus for sample injection into a torch comprising a manipulator and a liquid injection device, the liquid injection device comprising a first outlet; characterized in that the manipulator is arranged so that, in use, it can move the liquid injection device from a first position to a second position, the first position being such that the first outlet is aligned so that ejected liquid may enter the torch, the second position being such that the first outlet is positioned so as to be in fluid communication with a vessel.

15. The apparatus of claim 14 wherein the liquid injection device further comprises a second outlet, the apparatus further comprising a conduit having one end attached to the second outlet and the conduit having a second end attached to a pump, the pump being arranged so that in use it can both provide suction (negative pressure) or positive pressure to the conduit.

16. The apparatus of claim 14 wherein the manipulator is arranged so that, in use, it can move the liquid injection device from the first position to a third position and it can move the liquid injection device from the third position to a fourth position.

17. The apparatus of claim 14 wherein the liquid injection device is a micro-dispenser configured to eject single droplets less than 100 um in diameter.

18. The apparatus of claim 17 wherein the micro-dispenser comprises one of: a piezo-actuated droplet generator, a thermal inkjet device, a monodisperse dried microparticulate injector, a vibrating orifice monodisperse aerosol generator, a continuous fluid jet microdroplet generator, a flow focusing injector.

19. The apparatus of claim 14 further comprising a desolvator located between the first outlet of the liquid injection device when the liquid injector is in the first position, and the torch.

20. The apparatus of claim 14 further comprising a gas entrainment device located between the liquid injection device when the liquid injector is in the first position, and the torch.

21. The apparatus of claim 14 further comprising a plurality of similar or dissimilar liquid injection devices and wherein the manipulator is arranged so that in use it can move any of the liquid injection devices.

22. The apparatus of claim 14 further comprising a controller arranged so that in use it may control the apparatus.

23. The apparatus of claim 14 further comprising an inductively coupled plasma optical emission or mass spectrometer, or a microwave induced plasma optical emission or mass spectrometer, or an atomic absorption spectrometer or an atomic fluorescence spectrometer.

24. The apparatus of claim 23 further comprising a controller arranged so that in use it may control the apparatus and a computer having an input for receiving data from the spectrometer indicative of the progress of sample analysis and/or an input for receiving data which includes information about individual emitted droplets, and an output for outputting control signals to the controller and wherein the computer is programmed with a program comprising one or more modules of program code for deriving control signals to output to the controller.

* * * * *